US006489362B1

United States Patent
Teeter et al.

(10) Patent No.: US 6,489,362 B1
(45) Date of Patent: Dec. 3, 2002

(54) CARNITINE SUPPLEMENTED DIET TO PREVENT OR ALLEVIATE ASCITES IN BROILER TYPE POULTRY

(75) Inventors: Robert G. Teeter, Stillwater, OK (US); Stanley L. Vanhooser, Glencoe, OK (US); Kevin Q. Owen, Manhattan, KS (US)

(73) Assignees: The Board of Regents for Oklahoma State University, Stillwater, OK (US); Lonza, Inc., Fair Lawn, NJ (US)

( * ) Notice: Subject to any disclaimer, the term of this patent is extended or adjusted under 35 U.S.C. 154(b) by 0 days.

(21) Appl. No.: 09/273,653

(22) Filed: Mar. 23, 1999

(51) Int. Cl.⁷ .............................................. A61K 31/195
(52) U.S. Cl. ............................ 514/561; 424/442; 426/2
(58) Field of Search ............................ 426/2; 424/442; 514/561

(56) References Cited

U.S. PATENT DOCUMENTS

| | | |
|---|---|---|
| 4,075,352 A | 2/1978 | De Felice |
| 4,970,080 A | 11/1990 | Laurent et al. |
| 5,030,657 A | 7/1991 | Burtle et al. |
| 5,124,357 A | 6/1992 | Newton et al. |
| 5,192,804 A | 3/1993 | Blum et al. |
| 5,213,815 A | 5/1993 | O'Brien |
| 5,362,753 A | 11/1994 | Blum et al. |
| 5,516,798 A * | 5/1996 | Ferket ........................ 514/556 |
| 5,722,346 A | 3/1998 | Tremblay et al. |
| 6,090,849 A | 7/2000 | Teeter et al. |

FOREIGN PATENT DOCUMENTS

| | | | |
|---|---|---|---|
| DE | 195 28 076 A1 | 7/1997 | ............. A23K/1/18 |
| EP | 0 680 945 A2 | 11/1995 | ......... C07C/229/22 |
| IT | 1 248 867 | 1/1995 | |
| SU | 1790382 | * 7/1991 | |
| SU | 1678285 | * 9/1991 | |
| SU | 1743521 | * 6/1992 | |
| WO | WO 98/24328 | 6/1998 | |
| WO | WO 98/43617 | 10/1998 | |

OTHER PUBLICATIONS

Iben Wien. Tieraerztl. Monatsschr. (1997), 84(8), 228–232.*
Leibetseder Archiv fur Tierernahrung, (1995) 48 (1–2) 97–108.*
Rabie et al. Acta Biologica Hungarica '97(48) (2) pp. 221–239 & 241–252.*
Rabie et al British J. of Nutrition Oct. '97 78 (4) p. 615–623.*
Database WPI, Week 199528, May 16, 1995, Derwent Publications Ltd., London, GB; AN 1995–211576, XP002163197, Ajinomoto KK, Itochu Shiryo KK: "Disease preventive agents useful in poultry feed", Abstract.
Database WPI, Week 199640, Dec. 27, 1995, Derwent Publications Ltd., London, GB; AN 1996–400318, XP002141812, Boryaev G I, Galochkina V P, Kiselev A F: "Method of poultry growing" & RU 2 050 793 A ((GALO–I) Galochkina V P), Dec. 27, 1995, abstract.
Patent Abstract of Japan, vol. 013, No. 589 (C–670), Dec. 25, 1989 & JP 01 247046 A (Nippon Synthetic Chem Ind Co Ltd: THE), Oct. 2, 1989, abstract.
Luo Xiaoping; Reichetzer Barbara; Trines Jean; Benson Lee N; Lehotay Denis C: "L–carnitine attenuates doxorubicin–induced lipid peroxidation in rats.", Free Radical Biology & Medicine, vol. 26, No. 9–10, May 1999, pp. 1158–1165, XP000922670, abstract.
Shapir Y. et al: "Carnitine deficiency presenting as congestive heart failure." Children's Hospital Quarterly, (1992) 4/3 (169–172), XP000922641, abstract.
Rabie M H et al: "Effects of L–carnitine supplementation of diets differing in energy levels on performance, abdominal fat content, and yield and composition of edible meat of broilers.", British Journal of Nutrition, (Oct. 1998) 80 (4) 391–400, XP000922529, abstract.
Lettner V F; Zollitsch W; Halbmayer E: "Use of L–carnitine in the broiler ration" Bodenkultur, vol. 43, No. 2, 1992, pp. 161–167, XP000921440, abstract.

* cited by examiner

*Primary Examiner*—Neil Levy
(74) *Attorney, Agent, or Firm*—Fellers, Snider, Blankenship, Bailey & Tippens, P.C.

(57) ABSTRACT

An effective amount of carnitine is administered to broiler type poultry to prevent or alleviate ascites. In the preferred embodiment, a carnitine supplemented diet is fed to broiler type chickens in a feed composition during the phase of rapid tissue accretion where a high oxygen requirement stresses the birds' cardiovascular support system. The feed composition preferably contains between 5 and 1000 ppm of carnitine.

12 Claims, No Drawings

CARNITINE SUPPLEMENTED DIET TO PREVENT OR ALLEVIATE ASCITES IN BROILER TYPE POULTRY

BACKGROUND OF THE INVENTION

1. Field of Invention

The present invention relates generally to disease prevention in livestock, and, more specifically, to the prevention or alleviation of ascites in broiler type poultry.

2. Background

Ascites, also known as pulmonary hypertension syndrome, is a condition characterized by the accumulation of serous fluid in the spaces between tissues and organs in the abdominal cavity and is most prevalent as an affliction of poultry. The fluid is clear or amber in color, originates from the liver and has the general composition of plasma. Also referred to as waterbelly, high altitude disease and avian edema, ascites is attributable to the inability of the cardiovascular system to meet tissue oxygen demands.

The economic consequences associated with ascites are severe and occur due to a combination of increased bird mortality and condemnations along with reduced growth rate and feed efficiency. In the United States alone, annual poultry industry losses due to ascites are estimated to exceed 65 million dollars. Though estimates for dollar losses in other countries are not as readily available, the annual global impact of this disease likely exceeds a billion dollars.

In most cases ascites is brought about by a divergent bird oxygen requirement and its cardiovascular ability to supply oxygen as a nutrient. The inability of the cardiovascular system to meet tissue oxygen demands may result from may different circumstances, one example of which is a reduced atmospheric oxygen concentration. It was under these conditions in the 1970's that ascites was first recognized as a disease in broiler flocks grown at high altitude in South Africa and South America. Birds initially compensate for reduced tissue oxygen supply by increasing cardiac output. However, problems arise when the return blood volume exceeds the capacity of the heart to pump the blood. As a result, the heart enlarges, becomes round in outline and develops a dilated right ventricle. The right heart failure causes increased vena cava pressure and liver congestion. Classic ascites ensues due to the increased hepatic hydrostatic pressure resulting in transudation of fluid through the liver capsule into the abdominal cavity. The chronically elevated intrahepatic pressure leads to loss of hepatic parenchyma, intrahepatic fibrosis (cirrhosis) and hepatic dysfunction.

Other factors contributing or predisposing poultry to ascites have been identified. Pulmonary tissue damage, such as caused by exposure of birds to dust and ammonia, as well as diseases affecting the lungs (e.g., infectious bronchitis, Newcastle disease, infectious coryza, colibacillosis, aspergillosis), is known to be associated with an increased incidence of ascites, as is reduced cardiac function. Excess furazolidone, toxic fat and excess salt in the diet are also predisposing factors, along with cold distress brought about by nonevaporative heat loss.

Despite a better understanding of the disease, there has been a dramatic rise in ascites incidence in recent years. Primarily responsible is the increased growth rate of today's genetically engineered birds. The desire to achieve rapidly growing lean strains of meat chickens and the demands from processors to increase yields by reducing the overall size of visceral organs has meant a selection of strains susceptible to ascites. To put it in perspective, the age to slaughter and the amount of feed required to produce a given quantity of chicken meat has been more than halved since the early 1950's. See Havenstein, G. B., P. R. Ferket, S. E. Scheldeler and B. T. Larson, *Growth, Livability and Feed Conversion of 1957 vs. 1991 Broilers When Fed "Typical"* 1957 and 1991 *Broiler Diets, Poultry Science*, Vol. 73, pp. 1785–1794 (1994). In the early 1950's the average length of time required to grow a broiler chicken to a 4 pound harvest weight exceeded 15 weeks. Through genetic selection, this time period has been reduced to a current average of about 6 weeks. Consequently, bird metabolic events that are needed to produce a unit of poultry meat have been squeezed into a shorter time period, creating a high metabolic demand in today's bird. Such metabolic demand is further elevated by environmental factors, such as low and high ambient temperature, and disease. As a bird having a high metabolic demand possesses a higher oxygen requirement, severe stress is placed on the bird's cardiovascular support system. The stress is exacerbated when gain composition consists primarily of protein gain, as is the case with broiler type birds. Studies by the inventors show that trial broilers consumed 3.1 liters of oxygen per gram of protein gain versus just 0.82 liters of oxygen per gram of fat over a 35 day production period. Thus, a bird's ability to consume and transport oxygen not only has the potential to impact bird health via ascites, but also carcass composition by limiting protein synthesis ability.

The incidence of ascites in fast growing birds may be reduced by lowering gain accretion rate, such as by feeding low caloric density rations and restricting feed intake; however, lowering growth rate is not appealing to the poultry industry as it fails to maximize bird productivity.

There is thus a need for an aid to prevent or alleviate ascites in stressed, rapidly growing livestock, particularly poultry. The present inventors have discovered such an aid in a carnitine supplemented diet for poultry. The diet is unexpectedly effective at reducing the incidence of ascites (as evidenced in a reduced hematocrit, right ventricle weight and ascites heart ratio) in broiler type poultry and potentially enhances growth rate, feed efficiency, survivability and carcass quality.

In the patent art, U.S. Pat. No. 5,213,815 discloses a method of treating ascites comprising the administration of Eyebright herb and Brewer's yeast to poultry in need thereof. In U.S. Pat. No. 4,970,080, ascites is purportedly treated by feeding small amounts of zeolite to the affected animal.

Heretofore, carnitine in poultry diet has been reported to have no beneficial effect on feed intake, body and abdominal fat weight or on carcass or liver lipid levels in growing broilers (Cartwright, *Poultry Science*, Vol. 65, Suppl. 1, p. 21, 1986). Dietary carnitine has been shown to retard ethanol metabolism in broilers (Smith et al., *Poultry Science*, Vol. 71, Suppl. 1, p. 64, 1992), and, in U.S. Pat. No. 5,362,753, to increase the hatchability of eggs.

Unrelated to poultry, carnitine has been used as a supplement in pig diets (U.S. Pat. Nos. 5,124,357 and 5,192,804 and PCT Publication WO 98/24328), a smolting feed for salmon (U.S. Pat. No. 5,722,346) and in a catfish diet (U.S. Pat. No. 5,030,657). The use of carnitine in the treatment of heart failure or myocardial ischemia is discussed in U.S. Pat. No. 4,075,352 and PCT Publication WO 98/43617.

Notwithstanding the known uses of carnitine, the prior art wholly fails to teach or suggest as disclosed and claimed herein a carnitine supplemented diet fed to broiler type poultry to prevent or alleviate ascites.

BRIEF SUMMARY OF THE INVENTION

In connection with the present invention, an effective amount of carnitine is administered to broiler type poultry to prevent or alleviate ascites. Preferably, L-carnitine is administered as a supplement to the birds' food or water supply. Application in a feed composition is most preferred, wherein the amount of L-carnitine provided is between 5 to 1000 parts per million (ppm), and most preferably about 10–400 ppm, of the feed composition.

In one preferred aspect of the invention, the carnitine supplemented diet is fed to broiler type poultry between 0 and 18 weeks of age during the early life phase of rapid tissue accretion where a high oxygen requirement stresses the birds' cardiovascular support system.

In a particularly preferred aspect of the invention the carnitine supplemented diet is fed to broiler type chickens. In this respect, the carnitine supplemented diet is provided to broiler chickens between 0 and 11 weeks of age that have a live weight of up to 12 pounds, and, most preferably, to broiler type chickens between 0 and 7 weeks of age and weighing up to 7 pounds. While these parameters represent the current best mode and preferred embodiment for carrying out the present invention, it should be understood that because poultry industry goals focus on a one-tenth pound per year increase in bird weight, the years to come may see even greater bird growth rates and harvest weights.

A better understanding of the present invention and its objects and advantages will become apparent to those skilled in this art from the following detailed description, wherein there is described only the preferred embodiment of the invention, simply by way of illustration of the best mode contemplated for carrying out the invention. As will be realized, the invention is capable of modifications in various obvious respects, all without departing from the scope and spirit of the invention. Accordingly, the description should be regarded as illustrative in nature and not as restrictive.

DETAILED DESCRIPTION OF THE PREFERRED EMBODIMENT

Carnitine, chemically known as 3-hydroxy-4-N-trimethylaminobutyric acid or, alternatively, β-hydroxy-γ-trimethylaminobutyric acid, is a quaternary ammonium compound present in vertebrate muscle whose metabolic function involves the transfer of fatty acids across mitochondrial membranes. Like many other biological molecules, carnitine comes in two forms: L-carnitine and D-carnitine. As used herein the term "carnitine" refers to L-carnitine and/or pharmaceutically acceptable non-toxic salts thereof, non-limiting examples of which are tartrate, fumerate and magnesium citrate.

The preferred embodiment of the present invention involves the use of carnitine as a dietary supplement in broiler type poultry experiencing a high metabolic demand for energy due to high rate tissue accretion to prevent or alleviate ascites. The term "poultry" is used herein in its normal broad sense, referring to birds of several species, including chickens, turkeys, ducks, geese, swans, guineas, pigeons, peafowl, ostriches, pheasants, quail and other game birds. The term "broiler" refers to a subset of each species of poultry consisting of meat-type birds (i.e., birds produced for human consumption), well known in the industry, of an age generally between 0–18 weeks, depending upon the species of bird. Turkeys, for example, are generally grown to an older age than chickens. The inventors have surprisingly discovered that a carnitine supplemented diet fed to broiler type poultry during periods of high metabolic stress where the bird's oxygen requirement is elevated reduces the incidence of ascites as reflected in decreased values in bird hematocrit, right ventricle weight and ascites heart ratio. The theorized mode of action is the enhancement of lipid energy utilization within the heart for the generation of ATP and enhanced cardiac contractile function. Feeding the inventive diet should enhance feed efficiency and bird survivability while reducing condemnations within the processing plant.

The present invention is particularly suitable for use with all young meat-type chickens.

Broiler chickens are generally marketed at 5–7 weeks of age at a live weight of 4–7 pounds, although some, sometimes called "roaster" chickens, are marketed at 8–11 weeks of age at live weights between 7 and 12 pounds. For purposes of this application, however, all meat-type chickens are encompassed within the generic term "broilers" defined above. The term also encompasses poultry specialty products, such as so-called "Cornish hens," harvested at about 18 days of age at a weight of 1–1.5 pounds. From the time of hatch until harvest, these birds have a metabolizable energy requirement (from 2700–3300 kcal/kg ration) and concomitant oxygen demand that, in many cases, exceeds the capacity of the bird's cardiovascular system. Birds whose cardiovascular systems cannot handle the increased oxygen requirement brought on by rapid tissue accretion in this growth phase of the life cycle are prone to contract the ascites condition. Providing birds with a carnitine supplemented diet during this period of high metabolic demand has been shown to reduce the ascites incidence by lowering right ventricular weight and the ascites heart ratio, a known indicator for ascites susceptibility, and to also lower blood hematocrit, a variable that is correlated with ascites occurrence.

In connection with the present invention, supplemental carnitine is provided to broiler type poultry in a prophylactic or therapeutically effective amount, where the desired effect is a decrease in the incidence of ascites. This decrease can be of any level below the disease incidence of broiler type poultry fed a diet without the carnitine supplement.

It is preferred that the supplemental carnitine be provided in the diet of broiler type poultry, in either solid or liquid form, and, most preferably, as part of a feed composition. The necessary concentration of carnitine for a particular species and breed of poultry being fed may be optimized by one of ordinary skill by testing a range of carnitine concentrations using trial feed compositions.

In the case of broiler chickens, an effective amount of carnitine will range from about 5 ppm of the feed composition upwards. While no upper limit has been established as being counterproductive to the aims of the present invention (for convenience an upper range of 1000 ppm is suggested), the best known mode to practice the invention currently contemplates feeding a carnitine supplemented diet to broiler type chickens wherein the effective amount of carnitine is from about 10 ppm to about 400 ppm of the feed composition, and, most preferably, about 40 ppm of the feed composition.

The basal diet to which the carnitine is added can be any typical poultry diet meeting the nutritive needs of the broiler type bird, including starter, grower and finishing rations. A conventional diet includes selections among various protein, carbohydrate, vitamin and mineral sources and will generally contain about 12–25% crude protein, 0.5–10% crude fat and 2–12% crude fiber. The primary component is generally grain and processed grain by-products which supply carbohydrates and some protein. Protein meals from soybeans, alfalfa, corn gluten, cottonseed, sunflowers and other plants are often used to supply additional protein to the diet, as are animal by-products. Poultry feed compositions are generally supplemented with various vitamins and minerals, and molasses and animal fats are added to improve palatability and to increase or balance energy levels. General reference is made to National Research Council, *Nutrient Requirements of Poultry. Nutrient Requirements of Domestic Animals.* National Academy of Science, Washington, D.C. (1994), for a discussion of poultry nutrient requirements and typical poultry rations for various species and life phases of poultry, said reference being incorporated herein. Typical rations are also given below in connection with the reported examples. The feed schedule and feed rates can also be any standard schedule and rate used in the art.

As carnitine is water soluble, it alternatively may be administered through the bird's water supply. However, as water consumption varies according to the type of feed consumed, temperature, humidity, and activity of the bird, intake must be carefully monitored. The ratio of water to feed consumption in chickens generally ranges from 1.5–3.0 to 1, but may exceed 4-1 during high ambient temperature exposure or during periods of prolonged stress.

The present invention will be further understood by reference to the following non-limiting example.

EXAMPLE

Materials and Methods: Male Cobb-500 broiler chicks (obtained from Cobb Vantress of Siloam Springs, Ark.) were used. The chicks were divided into 24 groups of 4 and 24 groups of 9 chicks and randomly assigned to 60 open circuit respiratory chambers in three separate rooms. The chambers were housed in 3 thermostatically controlled rooms with 24 hour fluorescent light. Two levels of carnitine (0,200 ppm) were added to the basal diets (Table 1) and examined at two oxygen levels (17 and 20.6%).

TABLE 1

Composition of Basal Diets

| Ingredients | Basal 1 (%) | Basal 2 (%) | Basal 3 (%) | Basal 4 (%) |
|---|---|---|---|---|
| Corn/grd | 56.51 | 46.51 | 63.52 | 52.54 |
| Soybean meal/sol | 34–40 | 34.59 | 31.96 | 36.32 |
| Vegetable oil | 3.54 | 3.11 | 0.54 | 0.74 |
| Dicalcium phosphate | 1.67 | 1.68 | 1.66 | 1.67 |
| Limestone | 1.40 | 1.42 | 1.41 | 1.41 |
| Salt | 0.42 | 0.43 | 0.41 | 0.41 |
| Vit mix[1] | 0.20 | 0.20 | 0.20 | 0.20 |
| Trace mineral mix[2] | 0.11 | 0.11 | 0.11 | 0.11 |
| DL-Methionine (99%) | 0.16 | 0.10 | 0.20 | 0.06 |
| Corn gluten meal | 1.58 | 11.85 | — | 6.53 |
| ME(kcal/kg) | 2785.9 | 2806 | 2591.4 | 2606.5 |
| CP % | 19.9 | 24.8 | 18.53 | 23.06 |

[1]Mix supplied the following per lb: Vit A, 9,200,000 IU; Vit. D3, 2,800,000 IU; Vit. E, 21,700 IU; Vit. K, 2,600 mg; Thiamine, 2,000 mg; Riboflavin, 7,000 mg; Niacin, 54,700 mg; Pantothenic Acid, 11,300 mg; Pyradoxine, 3,400 mg; Vit. B12, 15.1 mg; Folic Acid, 967 mg; Biotin, 115 mg.
[2]Mix supplied the following per kilogram: Manganese, 120 mg; Zinc, 100 mg; Copper, 10 mg; Iodine, 2.5 mg; Calcium, 135 mg; Iron, 75 mg; Selenium, 0.15 mg.

Feed and drinking water were provided for ad-libitum consumption. Chamber temperature was maintained at 30° C. the first 5 days of age and at 27.8° C. thereafter. Chambers were checked twice daily for bird mortality. Body weights of each chick were obtained on day 0, 7 and 14. Feed consumption was determined on a chamber basis at the end of 1 and 2 weeks and feed efficiency calculated. Oxygen consumption and $CO_2$ production was recorded continuously on all chambers. Five birds at the start of the experiment were sacrificed for determination of initial composition. At the end of the experiment (Week 2) blood samples were taken from the wing vain of all birds for hematocrit determination. Heart weight and right ventricular mass of each bird were measured and the carcass saved for determination of lean and fat tissue gain using a Hologic densitometer.

Breathing Air Supply and Analysis: Compressed dried air (7% relative humidity (RH), 20.6% $O_2$) was delivered to chicks in the chamber via polyethylene tubes. It was necessary to provide low RH air to the chick chamber in order to hold the chamber at RH below 75%. The concentration of $O_2$ and $CO_2$ in air exiting each bird's chamber was monitored each day using Ametek oxygen (accuracy±0.02%) and carbon dioxide (accuracy±.03%) analyzers, respectively.

Statistical Analysis: Data were analyzed using the General Linear Model procedure of SAS (SAS, 1985). When a significant F statistic was noted by ANOVA, treatment means were compared using least square analysis variance.

Table 2 reports the results of this example.

TABLE 2

Feed consumption, body weight gain, gain:feed ratio, hematocrit, right ventricular weight and ascites heart index of broilers to 14 days of age fed diets with and without carnitine

| Parameter | Carnitine Level (ppm) | | ANOVA |
|---|---|---|---|
| | 0 | 200 | P |
| Feed (g/b) | 358 ± 8.4 | 352 ± 8.8 | 0.609 |
| Gain (g/b) | 261 ± 3.0 | 265 ± 3.1 | 0.343 |
| Gain:feed | 0.73 ± 0.0 | 0.76 ± 0.0 | 0.279 |
| HCT (%) | 36.11 ± 0.26 | 35.41 ± 0.24 | 0.048 |
| RV (g) | 0.21 ± 0.005 | 0.20 ± 0.006 | 0.043 |
| AHR (%) | 11.45 ± 0.24 | 10.57 ± 0.26 | 0.012 |

As shown in Table 2, carnitine supplementation in the broiler type chickens had a positive influence on the three primary indicators for ascites predisposition—hematocrit (HCT) value, right ventricle (RV) weight and acscites heart ratio (AHR). Hematocrit values are the most direct reflection of improved cardiac function, while right ventricle weight and ascites heart ratio, measured as the ratio of right ventricular mass to heart weight, facilitate the assessment of the cardiac traits associated with ascites. With the addition of 200 ppm of carnitine in the basal diet, hematocrit, right ventricle weight and ascites heart ratio were significantly decreased (P<0.05).

Further examples, conducted in the manner described above and reported below, showed a beneficial and significant lowering of hematcrit values for birds provided with carnitine supplemented diets at 12.5, 50 and 100 ppm carnitine.

TABLE 3

Hematocrit values of broilers fed carnitine supplemented diets

| Carnitine Level | HCT (%) | ANOVA P |
|---|---|---|
| 0 | 33.40 | |
| 12.5 | 32.11 | 0.099 |
| 50 | 31.99 | 0.071 |
| 100 | 30.60 | 0.0004 |

By benefitting the cardiac traits associated with ascites, the above results suggest that dietary carnitine is effective at reducing the incidence of ascites in broiler type poultry. The results further suggest providing supplemental carnitine to poultry during periods of high metabolic demand, and, specifically, to broilers undergoing high rate tissue accretion, such as genetically engineered birds. From the experimental data and with knowledge of the field it is reasonable to extrapolate an effective range of supplementation of between 5 and 1000 ppm.

In the most preferred embodiment carnitine is administered to broiler type poultry from birth through harvest as a prophylactic measure to prevent the onset of ascites. It is also contemplated, however, that carnitine supplementation may be initiated as a therapeutic remedy upon the detection of symptoms indicating the onset of the ascites syndrome. Such symptoms may include an elevated blood hematocrit, elevated ascites heart ratio, elevated ascites heart index (a parameter measured as a ratio of right ventricle weight to total ventricle weight and highly correlated to ascites heart ratio), a bluish comb color and/or bird panting. As used in this paragraph, "elevated" simply means a value higher than that considered in the field to be a normal value.

While the invention has been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

What is claimed is:

1. A method for therapeutically treating ascites in poultry among broiler birds between 0 and 18 weeks of age exhibiting symptoms thereof, which comprises supplementing the diet of said broiler birds with a composition consisting essentially of carnitine in an amount between 5 and 1000 ppm of the basal diet of said birds.

2. The method according to claim 1 wherein the carnitine is L-carnitine.

3. The method according to claim 1 further comprising feeding the carnitine to said broiler birds in a feed composition.

4. The method according to claim 1 wherein said broiler birds comprise chickens between 0 and 11 weeks in age and of a live weight of up to 12 pounds.

5. The method according to claim 3 wherein the amount of carnitine is about 10–400 ppm of the feed composition.

6. The method according to claim 5 wherein the amount of carnitine is about 40 ppm of the feed composition.

7. The method according to claim 1 further comprising providing the carnitine to said broiler birds via a water supply.

8. The method according to claim 4 wherein said chickens are between 0 and 7 weeks of age and of a live weight of up to 7 pounds.

9. The method according to claim 1, wherein said broiler birds have an oxygen demand that exceeds or nearly exceeds the capacity of the cardiovascular system to supply oxygen as a nutrient due to reduced oxygen availability.

10. The method according to claim 1, wherein said broiler birds have an oxygen demand that exceeds or nearly exceeds the capacity of the cardiovascular system to supply oxygen as a nutrient due to pulmonary tissue damage.

11. The method according to claim 1, wherein said broiler birds have an oxygen demand that exceeds or nearly exceeds the capacity of the cardiovascular system to supply oxygen as a nutrient due to cold distress.

12. The method according to claim 1, wherein said broiler birds have an oxygen demand that exceeds or nearly exceeds the capacity of the cardiovascular system to supply oxygen as a nutrient due to rapid tissue accretion.

* * * * *